(12) United States Patent
Kim et al.

(10) Patent No.: US 8,133,872 B2
(45) Date of Patent: Mar. 13, 2012

(54) USE OF NICOTINIC ACID ADENINE DINUCLEOTIDE PHOSPHATE OR DERIVATIVE THEREOF AS AGENT FOR TREATING TYPE-2 DIABETES

(75) Inventors: Uh Hyun Kim, Jeollabuk-do (KR); Kwang Hyun Park, Jeollabuk-do (KR); Myung Kwan Han, Jeollabuk-do (KR)

(73) Assignee: Industrial Cooperation Foundation, Chonbuk National University, Jeollabuk-do (KR)

( * ) Notice: Subject to any disclaimer, the term of this patent is extended or adjusted under 35 U.S.C. 154(b) by 290 days.

(21) Appl. No.: 12/468,600

(22) Filed: May 19, 2009

(65) Prior Publication Data

US 2009/0306006 A1 Dec. 10, 2009

(30) Foreign Application Priority Data

May 19, 2008 (KR) .................. 10-2008-0046335

(51) Int. Cl.
 *A61K 31/70* (2006.01)
 *C07H 19/207* (2006.01)
(52) U.S. Cl. .................. 514/43; 514/47; 536/26.24
(58) Field of Classification Search .................. None
See application file for complete search history.

(56) References Cited

OTHER PUBLICATIONS (R) Aarhus et al., "ADP-ribosyl Cyclase and CD38 Catalyze the Synthesis of a Calcium-mobilizing Metabolite from NADP," J. of Biological Chemistry, 270(51), 30327-30333 (Dec. 12, 1995).*
(S) Yamasaki et al., "Organelle Selection Determines Agonist-specific Ca2+ Signals in Pancreatic Acinar and β-Cells," J. of Biological Chemistry, 279(8), 7234-7240 (Feb. 2, 2004).*
(T) Johnson et al., "Nicotinic Acid-Adenine Dinucleotide Phosphate-sensitive Calcium Stores Initiate Insulin Signaling in Human Beta Cells," Proc. Natl. Academy of Sciences USA, 99(22), 14566-14571 (Oct. 29, 2002).*
Lacy et al., "Method for the Isolation of Intact Islets of Langerhans from the Rat Pancreas," *Diabetes*, vol. 16, No. 1, pp. 35-39 (Jan. 1967).
Aarhus et al., "ADP-ribosyl Cyclase and CD38 Catalyze the Synthesis of a Calcium-mobilizing Metabolite from NADP+," *The Journal of Biological Chemistry*, vol. 270, No. 51, pp. 30327-30333, Dec. 22, 1995.
Ämmälä et al., "Inositol trisphosphate-dependent periodic activation of a $Ca^{2+}$-activated $K^+$ conductance in glucose-stimulated pancreatic β-cells," *Nature*, vol. 353, pp. 849-852, Oct. 31, 1991.
Berridge et al., "Metabolism of the novel $Ca^{2+}$-mobilizing messenger nicotinic acid-adenine dinucleotide phosphate via a 2'-specific $Ca^{2+}$-dependent phosphatase," *Biochem. J. Vol.*, 365, pp. 295-301, 2002.
Cancela et al., "Regulation of Intracellular $Ca^{2+}$ Stores by Multiple $Ca^{2+}$-Releasing Messengers," *Diabetes*, vol. 51, Supplement 3, pp. S349-S357, Dec. 2002.
Chini et al., "CD38 is the major enzyme responsible for synthesis of nicotinic acid-adenine dinucleotide phosphate in mammalian tissues," *Biochem. J.*, 362, 125-130, 2002.
Churchill et al., "Spatial Control of $Ca^{2+}$ Signaling by Nicotinic Acid Adenine Dinucleotide Phosphate Diffusion and Gradients," *The Journal of Biological Chemistry*, vol. 275, No. 49, pp. 38687-38692, Dec. 8, 2000.
Delmeire et al., "Type VIII adenylyl cyclase in rat beta cells: coincidence signal detector generator for glucose and GLP-1," *Diabetologia*, vol. 46, pp. 1383-1393, 2003.
Hinke, et al., "Plasticity of the β cell insulin secretory competence: preparing the pancreatic β cell for the next meal," *J. Physiol.*, 558.2, pp. 369-380, 2004.
Holz, G., "New Insights Concerning the Glucose-dependent Insulin Secretagogue Action of Glucagon-like Peptide-1 in Pancreatic β-Cells," *Horm Metab Res.* 2004; 36(11-12): 787-794.
Holz et al., "Diabetes Outfoxed by GLP-1?" *Sci. STKE*; pp. 1-4, Jan. 25, 2005.
Johnson et al., "Nicotinic acid-adenine dinucleotide phosphate-sensitive calcium stores initiate insulin signaling in human beta cells," *PNAS*, vol. 99, No. 22, pp. 14566-1414751, Oct. 29, 2002.
Kang et al., "A cAMP and $Ca^{2+}$ coincidence detector in support of $Ca^{2+}$-induced $Ca^{2+}$ release in mouse pancreatic β cells," *J. Physiol.*, pp. 173-188, 2005.
Kato et al., "CD38 Disruption Impairs Glucose-induced Increases in Cyclic ADP-ribose, $[Ca^{2+}]i$, and Insulin Secretion," *The Journal of Biological Chemistry*, vol. 274, No. 4, pp. 1869-1872, Jan. 22, 1999.
Kato et al., "Regulatory Role of CD38 (ADP-ribosyl Cyclase/Cyclic ADP-ribose hydrolase) in Insulin Secretion by Glucose in Pancreatic β Cells," *The Journal of Biological Chemistry*, vol. 270, No. 50, pp. 30045-30050, Dec. 15, 1995.
Kieffer et al., "The Glucagon-Like Peptides," *Endocrine Reviews*, 2096), pp. 876-913, 1999.
Masgrau et al., "NAADP: A New Second Messenger for Glucose-Induced $Ca^{2+}$ Responses in Clonal Pancreatic β Cells," *Current Biology*, vol. 13, pp. 247-251, Feb. 4, 2003.
Okamoto, Hiroshi, "The CD38-cyclic ADP-ribose signaling system in insulin secretion," *Molecular and Cellular Biochemistry*, 193: 115-118, 1999.
Rah et al., "Activation of CD38 by Interleukin-8 Signaling Regulates Intracellular $Ca^{2+}$ Level and motility of Lymphokine-activated Killer Cells," *The Journal of Biological Chemistry*, vol. 280, No. 4, pp. 2888-2895, Jan. 28, 2005.
Rojas et al., "Control of Cytosolic Free Calcium in Cultured human Pancreatic β-Cells Occurs by External Calcium-Dependent and Independent Mechanisms," *Endocrinology*, vol. 134, No. 4, pp. 1771-1781, 1994. Rutter, Guy A., "Nutrient-secretion coupling in the pancreatic islet β-cell: recent advances," *Molecular Aspects of Medicine*, 22, pp. 247-284, 2001.
Takasawa et al., "Cyclic ADP-ribose and Inositol 1,4,5-Trisphosphate as Alternate Second Messengers for Intracellular $Ca^{2+}$ Mobilization in Normal and Diabetic β-Cells," *The Journal of Biological Chemistry*, vol. 273, No. 5, pp. 2497-2500, Jan. 30, 1998.
Togashi et al., "TRPM2 activation by cyclic ADP-ribose at body temperature is involved in insulin secretion," *The Embo Journal*, 25, pp. 1804-1815, 2006.
Wollheim et al., "Calcium-induced Insulin Release in Monolayer Culture of the Endocrine Pancreas," *The Journal of Biological Chemistry*, vol. 250, No. 4, Issue of Feb. 25, pp. 1354-1360, 1975.
Yamasaki et al., "Organelle Selection Determines Agonist-specific $Ca^{2+}$ Signals in Pancreatic Acinar and β Cells," *The Journal of Biological Chemistry*, vol. 279, No. 8, pp. 7234-7240, Feb. 20, 2004.

* cited by examiner

*Primary Examiner* — Lawrence E Crane
(74) *Attorney, Agent, or Firm* — Dickstein Shapiro LLP

(57) ABSTRACT

The administration of nicotinic acid adenine dinucleotide phosphate (NAADP) or a pharmaceutically acceptable salt thereof to a host in need thereof for the treatment of type-2 diabetes has been disclosed.

2 Claims, 3 Drawing Sheets

USE OF NICOTINIC ACID ADENINE DINUCLEOTIDE PHOSPHATE OR DERIVATIVE THEREOF AS AGENT FOR TREATING TYPE-2 DIABETES

CROSS REFERENCE TO RELATED APPLICATIONS

This application claims priority under 35 U.S.C. 119 to Application No. KR 10-2008-0046335, filed in the Republic of Korea on May 19, 2008.

BACKGROUND OF THE INVENTION

1. Field of the Invention

The present invention relates to a pharmaceutical composition comprising nicotinic acid adenine dinucleotide phosphate (NAAPD) or a derivative thereof useful for the treatment or prevention of type-2 diabetes (non-insulin-dependent diabetes mellitus; NIDDM)) or medical symptoms, which reduce the glucose threshold for insulin secretion, and to a method for treating type-2 diabetes using the compound. More specifically, the present invention relates to the use of nicotinic acid adenine dinucleotide phosphate or a derivative thereof as an agent for treating type-2 diabetes, because nicotinic acid adenine dinucleotide phosphate or a derivative thereof improves the insulin secretion ability of pancreatic β-islet cells isolated from normal mice (C57BL/6) and, when administered intraperioneally to type-2 diabetic mice, has excellent effects of lowering blood glucose levels and stimulating insulin secretion.

2. Description of the Prior Art

An increase in calcium concentration in beta-cells is attributable to extracellular calcium entry and rapid calcium release from extracellular calcium stores into the cytoplasm and induces insulin secretion (Wollheim C B et al., J Biol Chem 250:1354-1360, 1975., Rojas E. et al., Endocrinology 134:1771-1781, 1994., Cancela J M et al., Diabetes Suppl 3:S349-S357, 2002., Rutter G A., Mol Aspects Med 22:247-284, 2001).

An elevation in blood glucose levels stimulates insulin secretion through a specialized pathway that requires mitochondrial ATP synthesis, which leads to the closure of ATP-sensitive $K^+$ channels, the depolarization of cells and the entry of extracellular cells (Hinke S A et al., J Physiol 558: 369-380, 2004). Furthermore, a glucose-mediated elevation in calcium concentration is achieved through the following two calcium releasing receptors in the endoplasmic reticulum: $IP_3$ receptor for inositol 1,4,5-trisphosphate ($IP_3$) stimulated by $IP_3$/phospholipase C activation, and ryanodine receptor activated by cyclic ADP-ribose (cADPR) (Ammala C et al., Nature 353:849-852, 1991, Okamoto H., Mol Cell Biochem 193:115-118, 1999). Recent studies have indicated that cADPR also induces the entry of extracellular calcium (Rah S Y et al., J Biol Chem 280:2888-2895, 2005; Togashi K. et al., EMBO J. 25:1804-1815, 2006). It was reported that an additional pathway for the intracellular calcium release channel into the cytoplasm is the nicotinic acid adenine dinucleotide phosphate-sensitive receptor channel present in acidic lysosome-related granules (Churchill G C et al., J Biol Chem 275:38687-38692, 2000). Such cADPR and NAADP are synthesized by CD38 (Aarhus R et al., J Biol Chem 270:30327-30333, 1995; Chini E N et al., Biochem J 362:125-130, 2002). It was reported that glucose-stimulated calcium mobilization and insulin secretion are elevated by CD38 overexpression (Kato I et al., J Biol Chem 270:30045-30050, 1995) and reduced by CD38 knockout (Kato I et al., J Biol Chem 274: 1869-1872, 1999). Low levels of CD38 expression have been observed in diabetic β-cells isolated from an ob/ob mouse model and in RINm5F insulinoma cells with poor glucose-stimulated insulin production/release (Takasawa S et al., J Biol Chem 273:2497-2500, 1998). A recent study has indicated that NAADP initiates and propagates calcium signals in response to insulin and is involved in insulin synthesis (Johnson J D et al., Proc Natl Acad Sci USA 99: 14566-14571, 2002).

Along the same lines, NAADP-sensitive calcium store-controlled calcium signaling and the production of NAADP by glucose stimulus in β-cells have also been demonstrated (Masgrau R et al., Curr Biol 13:247-251, 2003; Yamasaki M et al., J Biol Chem 279:7234-7240, 2004).

Glucagon-like peptide-1 (GLP-1), a peptide hormone released from gut L-cells, is a physiologically important potentiator of glucose-induced insulin secretion (Kieffer T J and Habener J F: Endocr Rev 20:876-913, 1999; Holz G G and Chepurny O G, Sci STKE 2005(268):pe2, 2005). The peptide GLP-1 elevates intracellular cAMP concentrations and activates protein kinase A (PKA) and cAMP-regulated guanine nucleotide exchange factor II (cAMP-GEFII or Epac) (Delmeire D et al., Diabetologia 46:1383-1393, 2003; Kang G et al., J Physiol 566:173-188, 2005). Although these cAMP-binding proteins have been shown to play a role in GLP-1-mediated transient and sustained increase of calcium (Holz G G, Horm Metab Res 36:787-794, 2004), it remains to be clarified whether the increase of calcium is mediated through direct activation of calcium channels. In addition, the role of NAADP in calcium migration by PKA and Epac is not known, and the use of NAADP as an agent for treating diabetes is also not known.

In addition, Johnson J D et al. reported that nicotinic acid adenine dinucleotide phosphate increases insulin expression in beta-cells without increasing calcium, but does not increase insulin secretion (Johnson J D and Misler S., PNAS (2002) 99(22), 14566-14571).

SUMMARY OF THE INVENTION

Accordingly, the present inventors have found that nicotinic acid adenine dinucleotide phosphate, which regulates calcium signaling in β-cells, improves the insulin secretion ability of pancreatic β-islet cells isolated from mice and, when administered directly to C57BL/KsJ-db/db Jcl (known as type-2 diabetic mice), has excellent effects of lowering blood glucose levels and stimulating insulin secretion, thereby completing the present invention.

It is, therefore, an object of the present invention to provide the use of nicotinic acid adenine dinucleotide phosphate, a pharmaceutically acceptable salt thereof or a derivative thereof, which improve the insulin secretion ability of pancreatic β-islet cells and lowers blood glucose levels, as a novel agent for treating diabetes.

To achieve the above object, the present invention provides a pharmaceutical composition for preventing or treating type-2 diabetes, which comprises nicotinic acid adenine dinucleotide phosphate or a pharmaceutically acceptable salt or derivative thereof together with a pharmaceutically acceptable diluent or carrier.

The present invention also provides the use of NAADP or a pharmaceutically acceptable salt or derivative thereof in the preparation of a medicament for treating type-2 diabetes.

The present invention also provides a method for treating type-2 diabetes, which comprises administering an effective amount of NAADP or a pharmaceutically acceptable salt or derivative thereof to a mammal in need of such treatment.

In the present invention, the effective amount is preferably in the range of 0.1 to 1 mg/kg weight/day.

In the present invention, the administration is performed by intraperitoneal administration.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
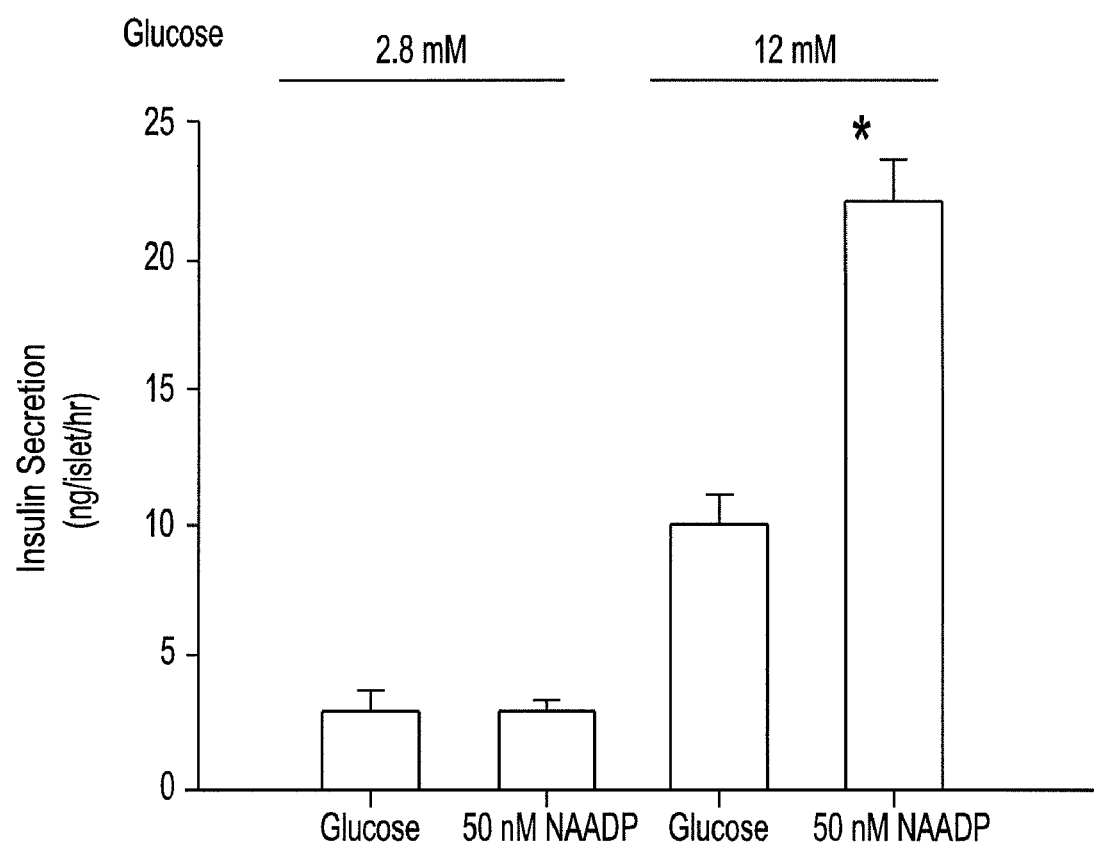
FIG. 1 is a graphic diagram showing the results obtained by isolating mouse pancreatic β-islet cells, treating the isolated cells with 0 nM and 50 nM of NAADP at extracellular glucose concentrations maintained at 2.8 mM and 12 mM, and then measuring the concentration of insulin secreted from the treated cells.

Hereinafter, the present invention will be described in detail.

Nicotinic acid adenine dinucleotide phosphate, which is used in the present invention, is produced by ADP-ribosyl cyclase, including CD38, in cells (Chini E N. et al., Biochem J 362:125-130, 2002; BERRIDGE G. et al., Biochem. J., 365: 295-301, 2002; Aarhus R. et al., J. Biol. Chem., 270(51): 30327-30333, 1995). NAADP, a compound which is used to regulate the concentration of calcium in the cells of all organisms, is critical to the maintenance of cellular biological events.

As seen in Examples below, the effect of NAADP against type-2 diabetes disease is demonstrated by a method comprising the steps of: isolating pancreatic islets from ICR mice according to the method of Lacy and Kotianovsky (Diabetes, 16, 35-39, 1967), treating the isolated islets with 2.8-12 mM of glucose alone or in combination with 0.5 μM-5 μM of NAADP, incubating the treated islets at 37° C. for 60 minutes, and then measuring insulin concentration in the supernatant, from which the pancreatic β-islet cells have been removed, using radioimmunoassay; administering NAADP to 7-week-old type-2 diabetic mice for 3 weeks and examining the effect of NAADP on blood glucose lowering; administrating NAADP intraperitoneally to 7-week-old type-2 diabetic mice for 3 weeks and measuring the insulin secretion ability of the mice; and analyzing the insulin secretion ability of pancreatic islet cells in control group mice and type-2 diabetic mice, administered with NAADP for 3 weeks, using an anti-insulin antibody by an immunohistochemical staining method.

ICR mice and C57BL/6 mice used in the present invention were purchased from Orientbio Inc. (Seongnam-si, Korea), and type-2 diabetic mice (C57BL/KsJ-db/db Jcl) were purchased from Jackson laboratory (USA). Also, NAADP and glucose used in the present invention were purchased from Sigma (USA). An insulin measurement kit used in the above step was purchased from Linco Research Inc. (USA).

In the above step, diabetic mice (C57BL/KsJ-db/db Jcl) were administered NAADP with an osmotic mini-pump (Alzet, USA) designed such that NAADP is continuously infused into the abdominal cavity of the mice at a dose of 0.1-1 mg/kg weight/day for 4 weeks using an osmotic mini-pump (Alzet, USA).

According to the present invention, there is provided a pharmaceutical composition for preventing and treating type-2 diabetes, which comprises NAADP and its pharmaceutically acceptable salts or derivatives together with a pharmaceutically acceptable diluent or carrier.

It is also to be understood that NAADP or its derivatives can exist in solvated as well as unsolvated forms such as, for example, hydrated forms.

Pharmaceutically acceptable derivatives of the compound of the present invention are represented by the following formula I:

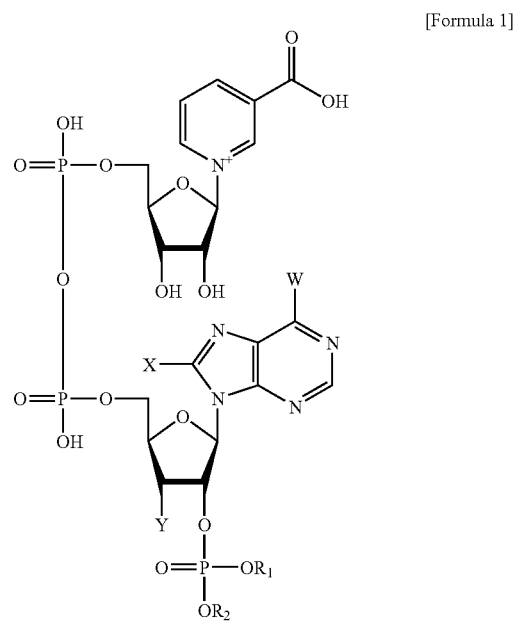

[Formula 1]

wherein $R_1$ and $R_2$ are the same or different and each represents

H or $CH_2$—$COCH_3$,

W is $NH_2$, OH or SH,

X is OH, SH, NH or Br, and

Y is OH, H, $NH_2$ or Br.

According to the present invention, there is also provided the use of NAADP or a pharmaceutically acceptable salt or derivative in the preparation of a medicament for treating type-2 diabetes.

The compound is suitably formulated as a pharmaceutical composition for use in this way.

According to another aspect of the present invention, there is provided a method for treating type-2 diabetes, which comprises administering NAADP or a pharmaceutically acceptable salt or derivative thereof to a mammal in need of such treatment.

Specific diseases which may be treated by the compound or composition of the present invention include: blood glucose lowering in type-2 diabetes without a serious risk of hypoglycemia (and potential to treat type-1 diabetes), dyslipidemia, obesity, insulin resistance, metabolic syndrome, and impaired glucose tolerance.

According to another aspect of the present invention, there is provided the use of NAADP or a pharmaceutically acceptable salt or derivative thereof in the preparation of a medicament for use in the treatment or prevention, particularly treatment, of obesity.

According to still another aspect of the present invention, there is provided NAADP or a pharmaceutically acceptable salt or derivative thereof as defined above for use as a medicament for treatment or prevention, particularly treatment, of obesity.

According to further aspect of the present invention, there is provided a method for the combined treatment of obesity and diabetes, which comprises administering an effective amount of NAADP or a pharmaceutically acceptable salt or derivative thereof to a mammal in need of such treatment.

According to further aspect of the present invention, there is provided a method for treating obesity, which comprises administering an effective amount of NAADP or a pharmaceutically acceptable salt or derivative to a mammal in need of such treatment.

The compounds of the present invention may be particularly suitable for use as pharmaceuticals because of advantageous physical and/or pharmacokinetic properties, and/or favorable toxicity profile.

A favorable toxicity profile may be demonstrated by use of an Ames test assay and/or by testing against the hERG ion channel. A favorable metabolic profile may mean, for example, reduced rate of metabolism, leading to reduction in clearance of the compound from the body and hence increased exposure to the compound, or a favorable metabolic profile may mean, for example, not forming active metabolites (which might be considered undesirable in some circumstances).

The composition of the present invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the present invention may be obtained by conventional procedures using conventional pharmaceutical excipients, well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the present invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of an active agent compounded with an appropriate and convenient amount of excipients which may vary from about 5% to about 98% by weight of the total composition. Dosage unit forms will generally contain about 1 mg to about 500 mg of an active ingredient.

The size of the dose for therapeutic or prophylactic purposes of NAADP or a pharmaceutically acceptable derivative thereof can be determined with reference to the following: 1) Anti-dyslipidaemia agents such as, HMG-CoA reductase inhibitors (e.g. statins); PPARα agonists (fibrates, e.g. gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations); 2) Antihypertensive agents such as, β-blockers (e.g. atenolol, inderal); ACE inhibitors (e.g. lisinopril); Calcium antagonists (e.g. nifedipine); Angiotensin receptor antagonists (e.g. candesartan), α-antagonists and diuretic agents (e.g. furosemide, benzthiazide); 3) Haemostasis modulators such as, anti-thrombotics, activators of fibrinolysis and antiplatelet agents; thrombin antagonists; factor Xa inhibitors; factor VIIa inhibitors); antiplatelet agents (e.g. aspirin, clopidogrel); antico-agulants (heparin and Low molecular weight analogues, hirudin) and warfarin; 4) Agents which antagonise the actions of glucagon; and 5) Anti-inflammatory agents, such as non-steroidal anti-inflammatory drugs (e.g. aspirin) and steroidal anti-inflammatory agents (e.g. cortisone). The preferred dose of NAADP or a pharmaceutically acceptable derivative thereof is in the range of 0.1 to 1 mg/kg/day.

As seen in Examples below, NAADP or a pharmaceutically acceptable derivative thereof according to the present invention improves the insulin secretion ability of pancreatic β-islet cells isolated from mice, and when NAADP or a pharmaceutically acceptable derivative thereof is administered to type-2 diabetic mice (C57BL/KsJ-db/db Jcl), it has excellent effects of lowering blood glucose levels and stimulating insulin secretion. Particularly, when NAADP is administered intraperitoneally at a dose of 0.1-1 mg/kg weight/day, it has excellent effects of stimulating insulin secretion and regulating blood glucose levels. Accordingly, it has an excellent effect of treating type-2 diabetes (non-insulin dependent diabetes mellitus (NIDDM)), and thus is very useful in the pharmaceutical industry.

EXAMPLE 1

Isolation of Pancreatic Islets from Mice and Improvement in Insulin Secretion Ability According to NAADP Treatment The isolation of pancreatic islets from six, 8-week-old ICR mice (Orientbio Inc., Seongnam-si, Korea) weighing 25-30 g was carried out according to the method of Lacy and Kotianovsky (Diabetes, 16, 35-39, 1967) in the following manner. Mice were sacrificed by cervical dislocation, and the peritoneum was incised. Hank's balanced salt solution (HBSS, Gibco, USA) containing 1 mg/mL of collagenase (Sigma, USA) was infused into the bile duct to inflate the pancreas, and then the pancreas was isolated. The isolated pancreas was incubated at 37° C. for 20 minutes, and then homogeneously agitated. The agitated solution was washed with HBSS to remove acinar cells, and then pancreatic islets of a given size were separated from the solution under stereoscopic binocular microscope. Ten isolated pancreatic islets were incubated with 2.8-12 mM glucose in 100 μl of Krebs Ringer bicarbonate buffer (Sigma, USA) containing 10 mM Hepes at 37° C. for 60 minutes, and then were treated with 0-5 μM NAADP (Sigma, USA). The concentration of insulin in the supernatant from which the pancreatic β-islet cells have been removed was measured. The measurement of the insulin concentration was carried out by radioimmunoassay using an insulin measurement kit (Diagnostic Products Corp., USA).

Insulin secretion from the mouse pancreatic β-islet cells after treatment by 0 nM and 50 nM at extracellular glucose concentrations maintained at 2.8 mM and 12 mM was measured, and the measurement results are shown in FIG. 1.

As shown in FIG. 1, when the pancreatic β-islet cells isolated from the mice were treated with 2.8-12 mM of glucose, low-concentration glucose (2.8 mM) had no effect on insulin secretion, but the group treated with high-concentration glucose (12 mM) showed a very high insulin secretion (FIG. 1). Accordingly, in the present invention, a glucose concentration of 12 mM at which high insulin secretion was induced was selected, and an increase in insulin secretion from β-islet cells was examined at various NAADP concentrations ranging from 0.5 nM to 5.0 μM. As a result, the group treated with 50 nM of NAADP showed a great increase in insulin secretion in the presence of glucose (12 mM) (FIG. 1).

Based on the above results, it was found that an NAADP concentration of 5-500 nM in the presence of glucose is essential for stimulating insulin secretion from pancreatic β-islet cells.

EXAMPLE 2

Effect of Long-Term Administration of NAADP on Blood Glucose Lowering

In this Example, the effect of long-term administration of NAADP on blood glucose lowering was examined.

Seven-week-old type-2 diabetic mice were divided into a control group (five animals) and test groups and tested using an osmotic mini-pump in the following manner. NAADP in an amount corresponding to a dose of 0 or 1 mg/kg/day was dissolved in 90 μl of sterile phosphate buffer saline and injected into the osmotic mini-pump using the enclosed needle and a disposable sterile syringe. Then, the NAADP solution was infused into the abdominal cavity of the mice according to the method described in the supplier's manual. The test results are shown in FIG. 2.

Figure 2:
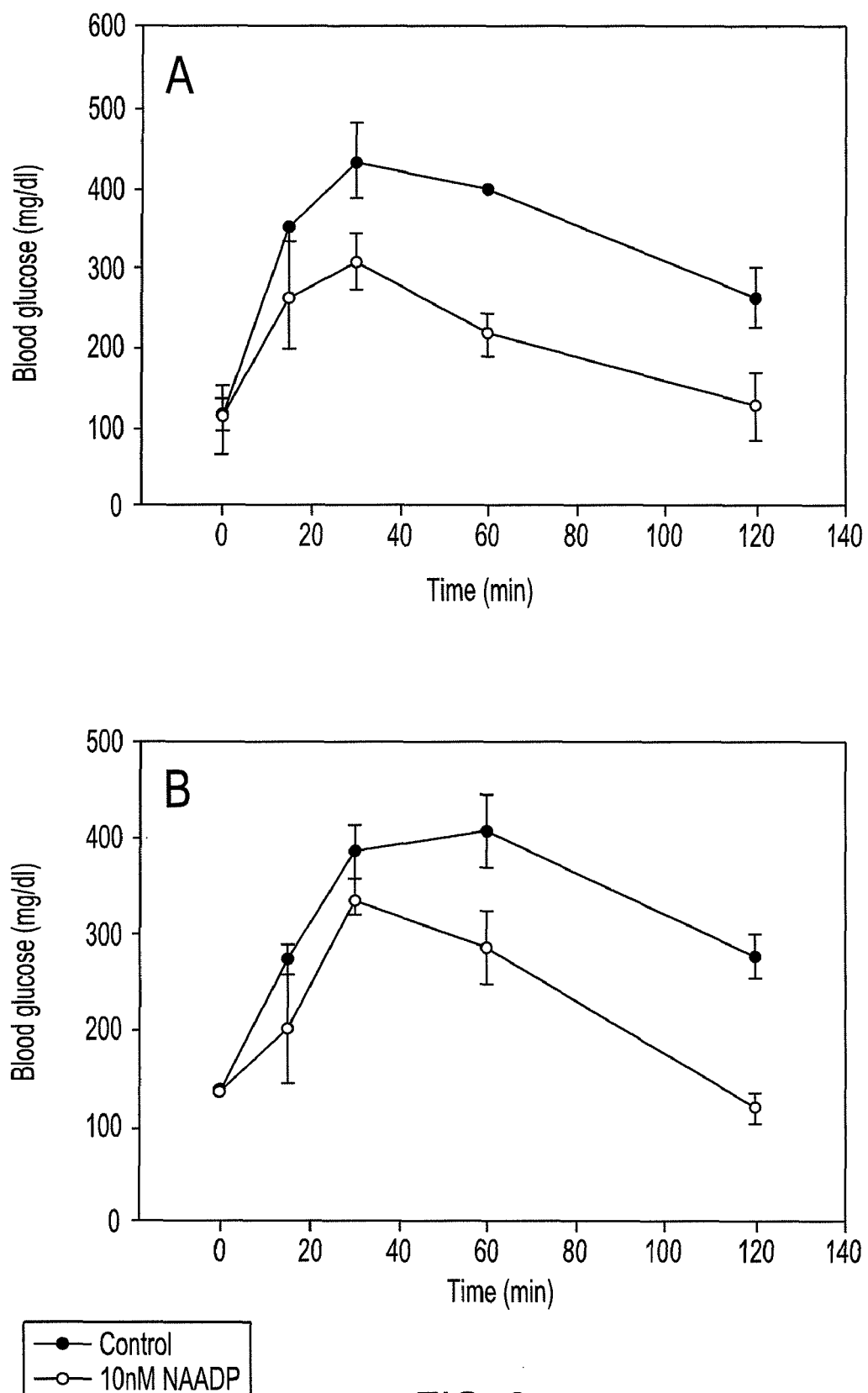
FIG. 2 is a graphic diagram showing the results of measurement of blood glucose concentration, obtained by administering NAADP to mice with an osmotic mini-pump constructed so as to maintain NAADP concentrations of 0-1 mg/kg/day, and then subjecting the mice to a glucose tolerance test at 2 weeks (9-week-old) and 3 weeks (10-week-old)

As shown in FIG. 2, when 0 or 1 mg/kg/day of NAADP was administered intraperitoneally to the type-2 diabetic mice for 3 weeks while measuring the mouse weight at 2 weeks (9-week-old) and 3 weeks (10-week-old), the mouse weight was increased with the passage of time, but there was no significant difference in weight between the test groups. However, the group administered with 1 mg/kg/day of NAADP showed a clear decrease in blood glucose levels.

The blood glucose-lowering effect of NAADP will now be described in detail. FIG. 2 shows the results obtained by measuring blood glucose levels after glucose load in the type-2 diabetic mice at 2 weeks and 3 weeks after administering 1 mg/kg/day of NAADP using the osmotic mini-pump.

The type-2 diabetic mice being administered with NAADP using the osmotic mini-pump were measured for blood glucose levels for 15-120 minutes after glucose load at a constant time interval on an empty stomach (fasting from 13 hours before testing). As a result, it was observed that, in the mouse group being administered with NAADP, the blood glucose level started to decrease from the peak at 30 minutes and returned to the fasting blood glucose level at 120 minutes.

Meanwhile, in the control group, the blood glucose level was not returned to the fasting blood glucose level even at 120 minutes after glucose load, suggesting that the control group lacked the ability to regulate blood glucose levels.

As can be seen from the foregoing, the 3-week intraperitoneal administration of up to 1 mg/kg/day of NAADP to the type-2 diabetic mice had a clear effect of lowering the blood glucose levels.

EXAMPLE 3

Effect of Administration of NAADP on Blood Insulin Secretion

In this Example, the effect of administration of NAADP on the change in blood insulin concentration was examined.

The same test method as described in Example 2 was used, and 50 µl of blood was collected from the tail vein just before glucose load. At 30 minutes (showing the highest blood glucose level after glucose load) and at 120 minutes (showing the lowest blood glucose level after glucose load), the same amount of blood was collected and coagulated, and serum was separated from the blood. The separated serum was measured for insulin concentration using an insulin RIA kit (Linco Research Inc., USA). The measurement results are shown in FIG. 3.

Figure 3:
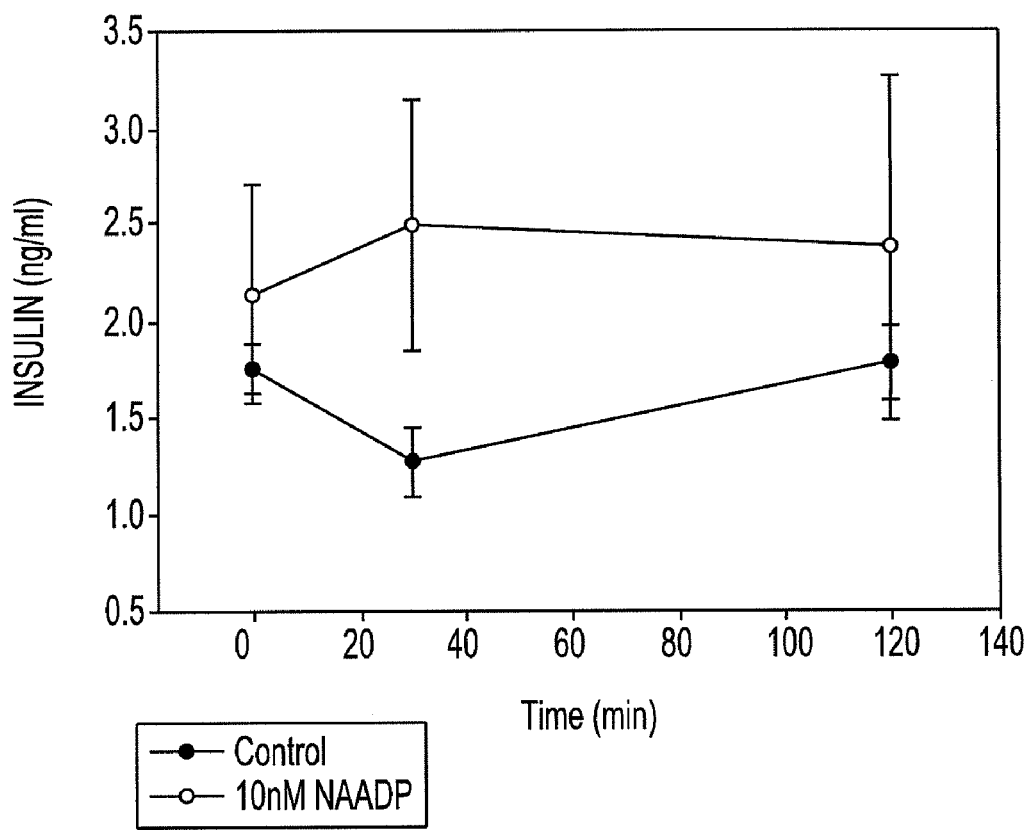
FIG. 3 is a graphic diagram showing the results of measurement of serum insulin secretion at various points of time, obtained by administering NAADP to mice with an osmotic mini-pump constructed so as to maintain NAADP concentrations of 0-1 mg/kg/day, and then subjecting the mice to a glucose tolerance test at 3 weeks (10-week-old)

As shown in FIG. 3, the type-2 diabetic mouse group administered with 1 mg/kg/day of NAADP showed a clear increase in blood insulin concentration at 3 weeks (10-week-old).

This effect of NAADP on the increase in insulin secretion will now be described in detail. FIG. 3 shows the results obtained by measuring blood insulin levels after glucose load in the type-2 diabetic mice at 3 weeks after administering 1 mg/kg/day of NAADP using the osmotic mini-pump.

The type-2 diabetic mice being administered with NAADP using the osmotic mini-pump were measured for insulin levels in sera collected at 0 min, 30 min and 120 min after glucose load on an empty stomach (fasting from 13 hours before testing). As a result, it was observed that, in the mouse group being administered with NAADP, the blood insulin level started to decrease from the peak at 30 minutes and was maintained at a constant level up to 120 minutes.

Meanwhile, in the control group of type-2 diabetic mice, the insulin concentration was slightly increased from the fasting insulin concentration at 120 minutes after glucose load; however, as described in Example 2, the control group did not have a sufficient ability to regulate blood glucose.

EXAMPLE 4

Examination of Insulin Secretion by Immunohistochemical Staining

In this Example, using a control group and type-2 diabetic mice administered with 1 mg/kg/day of NAADP for 3 weeks as described in Example 3, the insulin secretion ability of pancreatic islet cells was demonstrated using an anti-insulin antibody by immunohistochemical staining in order to prove that NAADP has an excellent effect of improving the insulin secretion ability.

Three mice, each administered with NAADP or phosphate buffer saline, were intraperioneally injected with 1 g/kg of glucose on an empty stomach. After 120 minutes, the mice were sacrificed by cervical dislocation, and then immediately the peritoneum was incised. Then, the intestinal and pancreatic tissues were collected and fixed in 4% paraformaldehyde solution (solvent-phosphate buffer; pH 7.4; Sigma, USA) for 12 hours or more. Then, the pancreatic tissue was separated from the intestinal or adipose tissue, and the separated tissue was washed three times or more with a fresh fixture and then processed into paraffin-embedded tissue according to a conventional method.

Tissue sections were cut from the paraffin-embedded tissue at 5-µm intervals using a microtome (Shandon, Germany) and applied to slides coated with poly-L-lysine (Sigma, USA) before use in immunohistochemical staining. In order to remove paraffin from the pancreatic tissue-coated slides, sections were deparaffinized with xylene (Junsei, Japan) for 5 minutes to remove paraffin. Then, the sections were hydrated in 100-70% alcohol series and allowed to stand in phosphate buffer (pH 7.4) for 5 minutes. Then, the sections were treated with 3% hydrogen peroxide to remove intrinsic peroxidase, and then allowed to react with anti-insulin antibody (Dako, USA) at 4° C. for 12 hours. Then, the section samples were subjected to immunohistochemical staining with anti-insulin antibody using an immunohistochemical staining kit (A.B.I., Jeonju-si, Korea).

The prepared tissue samples were counterstained with hematoxylin and viewed with an optical microscope (Leica, USA) at 100× objective, and the pancreatic islets were photographed at 200× magnification. To examine the pancreatic tissue, the samples were counterstained with hematoxylin-eosin (Sigma, USA).

Figure 4:
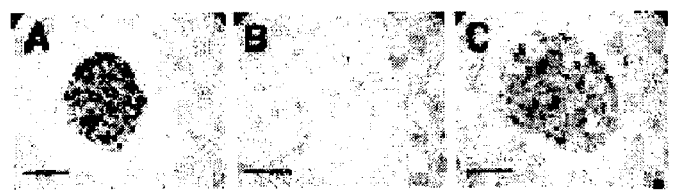
FIG. 4 is a set of photographs showing the results obtained by administering NAADP to type-2 diabetic mice with an osmotic mini-pump (constructed so as to maintain NAADP concentrations of 0-1 mg/kg/day) for 3 weeks, and then comparing insulin in pancreatic islet cells between normal mice and the type-2 diabetic mice using immunohistochemical staining (A: normal C57BL/6 mice; B: type-2 diabetic mouse group administered with saline; and C: type-2 diabetic mouse group administered with 1 mg/kg/day of NAADP).

The test results are shown in FIG. 4. As shown therein, in the hematoxylin-eosin staining of the control group administered with phosphate buffer for 4 weeks, the capsules covering the pancreatic islets were broken, and the density of the pancreatic β-islet cells was low. However, in the case of the test group administered with 1 mg/kg/day of NAADP for 3 weeks, the capsules covering the pancreatic islets and the .beta.-islet cells included in the capsules were clustered together.

Meanwhile, with respect to the insulin staining of the pancreatic β-islet cells by immunohistochemical staining, in the case of the control group administered with phosphate buffer for 3 weeks, the positive response of pancreatic β-islet cells to anti-insulin antibody was significantly decreased. However, in the case of the test group administered with 1 mg/kg/day of NAADP for 3 weeks, the positive response of pancreatic β-islet cells to anti-insulin antibody was clearly increased to the control group, suggesting that NAADP had an excellent effect of stimulating insulin secretion (FIG. 4).

As can be seen from the above result, the blood glucose lowering effect of NAADP, found in Example 2 when NAADP was administered to type-2 diabetic mice, was obtained because the drug NAADP had an excellent effect of stimulating insulin secretion.

As described above, NAADP or a pharmaceutically acceptable salt or derivative thereof according to the present invention improves the insulin secretion ability of pancreatic β-islet cells isolated from mice. In addition, when NAADP or a pharmaceutically acceptable salt or derivative thereof is administered to type-2 diabetic mice (C57BL/KsJ-db/db Jcl), it has excellent effects of lowering blood glucose levels and stimulating insulin secretion.

Although the preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method of treating type-2 diabetes, which comprises administering an effective amount of nicotinic acid adenine dinucleotide phosphate or a pharmaceutically acceptable salt thereof to a mammal in need of such treatment.

2. The method of claim 1, wherein the effective amount is in the range of 0.1 to 1 mg/kg weight/day.

* * * * *